(12) United States Patent
Misener et al.

(10) Patent No.: US 12,165,315 B2
(45) Date of Patent: Dec. 10, 2024

(54) ULTRASOUND SYSTEM WITH PRESSURE AND FLOW DETERMINATION CAPABILITY

(71) Applicant: Bard Access Systems, Inc., Salt Lake City, UT (US)

(72) Inventors: Anthony K. Misener, Bountiful, UT (US); Steffan Sowards, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 194 days.

(21) Appl. No.: 17/538,943

(22) Filed: Nov. 30, 2021

(65) Prior Publication Data
US 2022/0172354 A1 Jun. 2, 2022

Related U.S. Application Data

(60) Provisional application No. 63/120,053, filed on Dec. 1, 2020.

(51) Int. Cl.
*G06T 7/00* (2017.01)
(52) U.S. Cl.
CPC .. *G06T 7/0012* (2013.01); *G06T 2207/10132* (2013.01); *G06T 2207/20081* (2013.01);
(Continued)

(58) Field of Classification Search
None
See application file for complete search history.

(56) References Cited

U.S. PATENT DOCUMENTS

| 3,697,917 A | 10/1972 | Orth et al. |
| 5,148,809 A | 9/1992 | Biegeleisen-Knight et al. |

(Continued)

FOREIGN PATENT DOCUMENTS

| CN | 102871645 A | 1/2013 |
| CN | 105107067 B | 5/2018 |

(Continued)

OTHER PUBLICATIONS

U.S. Appl. No. 17/020,476, filed Sep. 14, 2020 Advisory Action dated Aug. 19, 2022.

(Continued)

*Primary Examiner* — Leon Flores
(74) *Attorney, Agent, or Firm* — Rutan & Tucker LLP

(57) ABSTRACT

An ultrasound imaging system is disclosed that includes an ultrasound probe including a plurality of ultrasound transducers configured to acquire ultrasound images, a processor and non-transitory computer-readable medium having stored thereon logic that, when executed by the processor, is configured to perform operations including receiving ultrasound imaging data, detecting one or more blood vessels within the ultrasound imaging data, identifying at least one blood vessel of the one or more blood vessels as an artery or as a vein, and rendering a visualization of at least a subset of the one or more blood vessels on a display. The logic may, when executed by the processor, cause performances of further operations including identifying the at least one blood vessel as the artery at least one differentiating characteristic of a plurality of differentiating characteristics of blood vessel type.

24 Claims, 5 Drawing Sheets

(52) U.S. Cl.
CPC ............... *G06T 2207/20084* (2013.01); *G06T 2207/30101* (2013.01)

(56) References Cited

U.S. PATENT DOCUMENTS

| | | | |
|---|---|---|---|
| 5,181,513 A | 1/1993 | Touboul et al. |
| 5,325,293 A | 6/1994 | Dorne |
| 5,349,865 A | 9/1994 | Kavli et al. |
| 5,441,052 A | 8/1995 | Miyajima |
| 5,549,554 A | 8/1996 | Miraki |
| 5,573,529 A | 11/1996 | Haak et al. |
| 5,775,322 A | 7/1998 | Silverstein et al. |
| 5,879,297 A | 3/1999 | Haynor et al. |
| 5,897,503 A | 4/1999 | Lyon et al. |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Haynor et al. |
| 6,233,476 B1 | 5/2001 | Strommer et al. |
| 6,245,018 B1 | 6/2001 | Lee |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,733,458 B1 | 5/2004 | Steins et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,038,619 B2 | 10/2011 | Steinbacher |
| 8,060,181 B2 | 11/2011 | Rodriguez Ponce et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,138,290 B2 | 9/2015 | Hadjicostis |
| 9,199,082 B1 | 12/2015 | Yared et al. |
| 9,204,858 B2 | 12/2015 | Pelissier et al. |
| 9,220,477 B2 | 12/2015 | Urabe et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,043,272 B2 | 8/2018 | Forzoni et al. |
| 10,449,330 B2 | 10/2019 | Newman et al. |
| 10,524,691 B2 | 1/2020 | Newman et al. |
| 10,751,509 B2 | 8/2020 | Misener |
| 11,564,861 B1 | 1/2023 | Gaines |
| 2002/0038088 A1 | 3/2002 | Imran et al. |
| 2003/0047126 A1 | 3/2003 | Tomaschko |
| 2003/0106825 A1 | 6/2003 | Molina et al. |
| 2003/0120154 A1 | 6/2003 | Sauer et al. |
| 2003/0125629 A1 | 7/2003 | Ustuner |
| 2003/0135115 A1 | 7/2003 | Burdette et al. |
| 2003/0149366 A1 | 8/2003 | Stringer et al. |
| 2004/0015080 A1 | 1/2004 | Kelly et al. |
| 2004/0055925 A1 | 3/2004 | Franks-Farah et al. |
| 2004/0197267 A1 | 10/2004 | Black et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |

(56) References Cited

U.S. PATENT DOCUMENTS

| | | |
|---|---|---|
| 2006/0004290 A1 | 1/2006 | Smith et al. |
| 2006/0013523 A1 | 1/2006 | Childlers et al. |
| 2006/0015039 A1 | 1/2006 | Cassidy et al. |
| 2006/0020204 A1 | 1/2006 | Serra et al. |
| 2006/0047617 A1 | 3/2006 | Bacioiu et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2006/0241463 A1 | 10/2006 | Shau et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0167738 A1 | 7/2007 | Timinger et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2007/0287886 A1 | 12/2007 | Saadat |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0108930 A1 | 5/2008 | Weitzel et al. |
| 2008/0125651 A1 | 5/2008 | Watanabe et al. |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0269605 A1 | 10/2008 | Nakaya |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0012401 A1 | 1/2009 | Steinbacher |
| 2009/0074280 A1 | 3/2009 | Lu et al. |
| 2009/0124903 A1 | 5/2009 | Osaka |
| 2009/0137887 A1 | 5/2009 | Shariati et al. |
| 2009/0137907 A1 * | 5/2009 | Takimoto ............... A61B 34/20 600/461 |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0281413 A1 | 11/2009 | Boyden et al. |
| 2009/0306509 A1 | 12/2009 | Pedersen et al. |
| 2010/0010348 A1 | 1/2010 | Halmann |
| 2010/0211026 A2 | 8/2010 | Sheetz et al. |
| 2010/0249598 A1 | 9/2010 | Smith et al. |
| 2010/0286515 A1 | 11/2010 | Gravenstein et al. |
| 2010/0312121 A1 | 12/2010 | Guan |
| 2010/0324423 A1 | 12/2010 | El-Aklouk et al. |
| 2011/0002518 A1 | 1/2011 | Ziv-Ari et al. |
| 2011/0026796 A1 | 2/2011 | Hyun et al. |
| 2011/0071404 A1 | 3/2011 | Schmitt et al. |
| 2011/0074244 A1 | 3/2011 | Osawa |
| 2011/0087107 A1 | 4/2011 | Lindekugel et al. |
| 2011/0166451 A1 | 7/2011 | Blaivas et al. |
| 2011/0282188 A1 | 11/2011 | Burnside et al. |
| 2011/0295108 A1 | 12/2011 | Cox et al. |
| 2011/0313293 A1 | 12/2011 | Lindekugel et al. |
| 2012/0165679 A1 | 6/2012 | Orome et al. |
| 2012/0179038 A1 | 7/2012 | Meurer et al. |
| 2012/0179042 A1 | 7/2012 | Fukumoto et al. |
| 2012/0179044 A1 | 7/2012 | Chiang et al. |
| 2012/0197132 A1 | 8/2012 | O'Connor |
| 2012/0220865 A1 | 8/2012 | Brown et al. |
| 2012/0277576 A1 | 11/2012 | Lui |
| 2013/0041250 A1 * | 2/2013 | Pelissier ................. A61B 8/461 600/424 |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0197367 A1 | 8/2013 | Smok et al. |
| 2013/0218024 A1 | 8/2013 | Boctor et al. |
| 2013/0323700 A1 | 12/2013 | Samosky et al. |
| 2013/0338503 A1 | 12/2013 | Cohen et al. |
| 2013/0338508 A1 | 12/2013 | Nakamura et al. |
| 2013/0345566 A1 | 12/2013 | Weitzel et al. |
| 2014/0005530 A1 | 1/2014 | Liu et al. |
| 2014/0031694 A1 | 1/2014 | Solek |
| 2014/0066779 A1 | 3/2014 | Nakanishi |
| 2014/0073976 A1 | 3/2014 | Fonte et al. |
| 2014/0100440 A1 | 4/2014 | Cheline et al. |
| 2014/0114194 A1 | 4/2014 | Kanayama et al. |
| 2014/0170620 A1 | 6/2014 | Savitsky et al. |
| 2014/0180098 A1 | 6/2014 | Flaherty et al. |
| 2014/0180116 A1 | 6/2014 | Lindekugel et al. |
| 2014/0188133 A1 | 7/2014 | Misener |
| 2014/0188440 A1 | 7/2014 | Donhowe et al. |
| 2014/0276059 A1 | 9/2014 | Sheehan |
| 2014/0276069 A1 | 9/2014 | Amble et al. |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2014/0357994 A1 | 12/2014 | Jin et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0141821 A1 | 5/2015 | Yoshikawa et al. |
| 2015/0190111 A1 | 7/2015 | Fry |
| 2015/0209113 A1 | 7/2015 | Burkholz et al. |
| 2015/0209510 A1 | 7/2015 | Burkholz et al. |
| 2015/0209526 A1 | 7/2015 | Matsubara et al. |
| 2015/0257735 A1 | 9/2015 | Ball et al. |
| 2015/0282890 A1 | 10/2015 | Cohen et al. |
| 2015/0294497 A1 | 10/2015 | Ng et al. |
| 2015/0297097 A1 | 10/2015 | Matsubara et al. |
| 2015/0342572 A1 | 12/2015 | Tahmasebi Maraghoosh et al. |
| 2015/0359520 A1 | 12/2015 | Shan et al. |
| 2015/0359991 A1 | 12/2015 | Dunbar et al. |
| 2016/0000367 A1 | 1/2016 | Lyon |
| 2016/0026894 A1 | 1/2016 | Nagase |
| 2016/0029995 A1 | 2/2016 | Navratil et al. |
| 2016/0113699 A1 | 4/2016 | Sverdlik et al. |
| 2016/0120607 A1 | 5/2016 | Sorotzkin et al. |
| 2016/0157831 A1 | 6/2016 | Kang et al. |
| 2016/0166232 A1 | 6/2016 | Merritt |
| 2016/0202053 A1 | 7/2016 | Walker et al. |
| 2016/0211045 A1 | 7/2016 | Jeon et al. |
| 2016/0213398 A1 | 7/2016 | Liu |
| 2016/0220124 A1 | 8/2016 | Grady et al. |
| 2016/0259992 A1 | 9/2016 | Knodt et al. |
| 2016/0278869 A1 | 9/2016 | Grunwald |
| 2016/0287214 A1 | 10/2016 | Ralovich et al. |
| 2016/0296208 A1 | 10/2016 | Sethuraman et al. |
| 2016/0374644 A1 | 12/2016 | Mauldin, Jr. et al. |
| 2017/0014105 A1 | 1/2017 | Chono |
| 2017/0020561 A1 | 1/2017 | Cox et al. |
| 2017/0079548 A1 | 3/2017 | Silverstein et al. |
| 2017/0143312 A1 | 5/2017 | Hedlund et al. |
| 2017/0164923 A1 | 6/2017 | Matsumoto |
| 2017/0172666 A1 | 6/2017 | Govari et al. |
| 2017/0215842 A1 | 8/2017 | Ryu et al. |
| 2017/0252004 A1 | 9/2017 | Broad et al. |
| 2017/0328751 A1 | 11/2017 | Lemke |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0228465 A1 | 8/2018 | Southard et al. |
| 2018/0235649 A1 | 8/2018 | Elkadi |
| 2018/0235709 A1 | 8/2018 | Donhowe et al. |
| 2018/0289927 A1 | 10/2018 | Messerly |
| 2018/0296185 A1 | 10/2018 | Cox et al. |
| 2018/0310955 A1 | 11/2018 | Lindekugel et al. |
| 2018/0344293 A1 | 12/2018 | Raju et al. |
| 2019/0060001 A1 | 2/2019 | Kohli et al. |
| 2019/0060014 A1 | 2/2019 | Hazelton et al. |
| 2019/0090855 A1 | 3/2019 | Kobayashi et al. |
| 2019/0125210 A1 | 5/2019 | Govari et al. |

(56) References Cited

U.S. PATENT DOCUMENTS

| | | |
|---|---|---|
| 2019/0200951 A1 | 7/2019 | Meier |
| 2019/0239848 A1 | 8/2019 | Bedi et al. |
| 2019/0307419 A1 | 10/2019 | Durfee |
| 2019/0307515 A1 | 10/2019 | Naito et al. |
| 2019/0365347 A1 | 12/2019 | Abe |
| 2019/0365348 A1 | 12/2019 | Toume et al. |
| 2019/0365354 A1 | 12/2019 | Du |
| 2020/0069929 A1 | 3/2020 | Mason et al. |
| 2020/0113540 A1 | 4/2020 | Gijsbers et al. |
| 2020/0163654 A1 | 5/2020 | Satir et al. |
| 2020/0200900 A1 | 6/2020 | Asami et al. |
| 2020/0229795 A1 | 7/2020 | Tadross et al. |
| 2020/0230391 A1 | 7/2020 | Burkholz et al. |
| 2020/0237403 A1 | 7/2020 | Southard et al. |
| 2020/0281563 A1 | 9/2020 | Muller et al. |
| 2020/0359990 A1 | 11/2020 | Poland et al. |
| 2020/0390416 A1* | 12/2020 | Swan ................... A61B 34/20 |
| 2021/0059639 A1 | 3/2021 | Howell |
| 2021/0077058 A1 | 3/2021 | Mashood et al. |
| 2021/0137492 A1 | 5/2021 | Imai |
| 2021/0161510 A1 | 6/2021 | Sasaki et al. |
| 2021/0186467 A1 | 6/2021 | Urabe et al. |
| 2021/0212668 A1 | 7/2021 | Li et al. |
| 2021/0267570 A1 | 9/2021 | Ulman et al. |
| 2021/0295048 A1 | 9/2021 | Buras et al. |
| 2021/0315538 A1 | 10/2021 | Brandl et al. |
| 2021/0378627 A1 | 12/2021 | Yarmush et al. |
| 2022/0039777 A1 | 2/2022 | Durfee |
| 2022/0039829 A1 | 2/2022 | Zijlstra et al. |
| 2022/0071593 A1 | 3/2022 | Tran |
| 2022/0096053 A1 | 3/2022 | Sethuraman et al. |
| 2022/0096797 A1 | 3/2022 | Prince |
| 2022/0104791 A1 | 4/2022 | Matsumoto |
| 2022/0104886 A1 | 4/2022 | Blanchard et al. |
| 2022/0117582 A1 | 4/2022 | McLaughlin et al. |
| 2022/0160434 A1 | 5/2022 | Messerly et al. |
| 2022/0168050 A1 | 6/2022 | Sowards et al. |
| 2022/0296303 A1 | 9/2022 | McLeod et al. |
| 2022/0330922 A1 | 10/2022 | Sowards et al. |
| 2022/0334251 A1 | 10/2022 | Sowards et al. |
| 2022/0361840 A1 | 11/2022 | Matsumoto et al. |
| 2023/0107629 A1 | 4/2023 | Sowards et al. |
| 2023/0132148 A1 | 4/2023 | Sowards et al. |
| 2023/0135562 A1 | 5/2023 | Misener et al. |
| 2023/0138970 A1 | 5/2023 | Sowards et al. |
| 2023/0148872 A1 | 5/2023 | Sowards et al. |
| 2023/0201539 A1 | 6/2023 | Howell |
| 2023/0277153 A1 | 9/2023 | Sowards et al. |
| 2023/0277154 A1 | 9/2023 | Sowards et al. |
| 2023/0293143 A1 | 9/2023 | Sowards et al. |
| 2023/0338010 A1 | 10/2023 | Sturm |
| 2023/0371928 A1 | 11/2023 | Rajguru et al. |
| 2023/0397900 A1 | 12/2023 | Prince |
| 2024/0065673 A1 | 2/2024 | Sowards et al. |

FOREIGN PATENT DOCUMENTS

| | | |
|---|---|---|
| EP | 0933063 A1 | 8/1999 |
| EP | 1504713 A1 | 2/2005 |
| EP | 1591074 B1 | 5/2008 |
| EP | 2823766 A1 | 1/2015 |
| EP | 3181083 A1 | 6/2017 |
| EP | 3870059 | 9/2021 |
| JP | 2000271136 A | 10/2000 |
| JP | 2007222291 A | 9/2007 |
| JP | 2014150928 A | 8/2014 |
| JP | 2018175547 A | 11/2018 |
| KR | 20180070878 A | 6/2018 |
| KR | 102176196 B1 | 11/2020 |
| WO | 2010029521 A2 | 3/2010 |
| WO | 2010076808 A1 | 7/2010 |
| WO | 2013059714 A1 | 4/2013 |
| WO | 2014/115150 A1 | 7/2014 |
| WO | 2015/017270 A1 | 2/2015 |
| WO | 2016081023 A1 | 5/2016 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020067897 A1 | 4/2020 |
| WO | 2020083660 A1 | 4/2020 |
| WO | 2020/186198 A1 | 9/2020 |
| WO | 2021198226 A1 | 10/2021 |
| WO | 2022/072727 A2 | 4/2022 |
| WO | 2022/081904 A1 | 4/2022 |
| WO | 2022/119853 A1 | 6/2022 |
| WO | 2022115479 A1 | 6/2022 |
| WO | 2022119856 A1 | 6/2022 |
| WO | 2022221703 A1 | 10/2022 |
| WO | 2022221714 A1 | 10/2022 |
| WO | 2023059512 A1 | 4/2023 |
| WO | 2023076268 A1 | 5/2023 |
| WO | 2023081220 A1 | 5/2023 |
| WO | 2023081223 A1 | 5/2023 |
| WO | 2023091424 A1 | 5/2023 |
| WO | 2023167866 A1 | 9/2023 |
| WO | 2023177718 A1 | 9/2023 |
| WO | 2024044277 A1 | 2/2024 |

OTHER PUBLICATIONS

U.S. Appl. No. 17/020,476, filed Sep. 14, 2020 Non-Final Office Action dated Sep. 23, 2022.
U.S. Appl. No. 17/471,015, filed Sep. 9, 2021 Non-Final Office Action dated Aug. 16, 2022.
PCT/US2022/025097 filed Apr. 15, 2021 International Preliminary Report on Patentability dated Oct. 26, 2023.
PCT/US2023/030970 filed Aug. 23, 2023 International Search Report and Written Opinion dated Oct. 30, 2023.
U.S. Appl. No. 17/468,318, filed Sep. 7, 2021 Advisory Action dated Nov. 6, 2023.
U.S. Appl. No. 17/468,318, filed Sep. 7, 2021 Notice of Allowance dated Jan. 18, 2024.
U.S. Appl. No. 17/534,099, filed Nov. 23, 2021 Advisory Action dated Dec. 8, 2023.
U.S. Appl. No. 17/538,911, filed Nov. 30, 2021 Advisory Action dated Nov. 22, 2023.
U.S. Appl. No. 17/684,180, filed Mar. 1, 2022 Final Office Action dated Jan. 18, 2024.
U.S. Appl. No. 17/722,111, filed Apr. 15, 2022 Non-Final Office Action dated Dec. 22, 2023.
U.S. Appl. No. 17/722,151, filed Apr. 15, 2022 Advisory Action dated Jan. 2, 2024.
U.S. Appl. No. 17/722,151, filed Apr. 15, 2022 Final Office Action dated Nov. 6, 2023.
U.S. Appl. No. 17/894,460, filed Aug. 24, 2022 Non-Final Office Action dated Nov. 6, 2023.
Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).
PCT/US2021/045218 filed Aug. 9, 2021 International Search Report and Written Opinion dated Nov. 23, 2021.
PCT/US2021/049123 filed Sep. 3, 2021 International Search Report and Written Opinion dated Feb. 4, 2022.
PCT/US2021/053018 filed Sep. 30, 2021 International Search Report and Written Opinion dated May 3, 2022.
PCT/US2021/060622 filed Nov. 23, 2021 International Search Report and Written Opinion dated Mar. 3, 2022.
PCT/US2021/061267 filed Nov. 30, 2021 International Search Report and Written Opinion dated Mar. 9, 2022.
PCT/US2021/061276 filed Nov. 30, 2021 International Search Report and Written Opinion dated Mar. 9, 2022.

(56) References Cited

OTHER PUBLICATIONS

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.
U.S. Appl. No. 15/951,903, filed Apr. 12, 2018 Board Decision dated Apr. 20, 2022.
U.S. Appl. No. 15/951,903, filed Apr. 12, 2018 Notice of Allowance dated May 2, 2022.
William F Garrett et al: "Real-time incremental visualization of dynamic ultrasound volumesusing parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
Pagoulatos, N. et al. "New spatial localizer based on fiber optics with applications in 3D ultrasound imaging" Proceeding of Spie, vol. 3976 (Apr. 18, 2000; Apr. 18, 2000).
PCT/US2022/025082 filed Apr. 15, 2022 International Search Report and Written Opinion dated Jul. 11, 2022.
PCT/US2022/025097 filed Apr. 15, 2022 International Search Report and Written Opinion dated Jul. 8, 2022.
U.S. Appl. No. 17/020,476, filed Sep. 14, 2020 Final Office Action dated Jun. 9, 2022.
EP 20866520.8 filed Apr. 5, 2022 Extended European Search Report dated Aug. 22, 2023.
U.S. Appl. No. 17/468,318, filed Sep. 7, 2021 Final Office Action dated Sep. 8, 2023.
U.S. Appl. No. 17/471,015, filed Sep. 9, 2021 Final Office Action dated Oct. 12, 2023.
U.S. Appl. No. 17/534,099, filed Nov. 23, 2021 Final Office Action dated Sep. 29, 2023.
U.S. Appl. No. 17/538,911, filed Nov. 30, 2021 Final Office Action dated Sep. 13, 2023.
U.S. Appl. No. 17/684,180, filed Mar. 1, 2022 Non-Final Office Action dated Jul. 28, 2023.
U.S. Appl. No. 17/722,151, filed Apr. 15, 2022 Non-Final Office Action dated Sep. 7, 2023.
PCT/US12/61182 International Seach Report and Written Opinion dated Mar. 11, 2013.
PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/052055 filed Sep. 24, 2021 International Search Report and Written Opinion dated Dec. 20, 2021.
U.S. Appl. No. 13/656,563, filed Oct. 19, 2012 Decision on Appeal dated Nov. 1, 2017.
U.S. Appl. No. 13/656,563, filed Oct. 19, 2012 Examiner's Answer dated Nov. 16, 2015.
U.S. Appl. No. 13/656,563, filed Oct. 19, 2012 Final Office Action dated Dec. 5, 2014.
U.S. Appl. No. 13/656,563, filed Oct. 19, 2012 Non-Final Office Action dated Jul. 18, 2014.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 15/951,903, filed Apr. 12, 2018 Advisory Action dated Dec. 22, 2020.
U.S. Appl. No. 15/951,903, filed Apr. 12, 2018 Examiner's Answer dated Jun. 3, 2021.
U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.
U.S. Appl. No. 17/020,476, filed Sep. 14, 2020 Non-Final Office Action dated Feb. 9, 2022.
PCT/US2023/014143 filed Feb. 28, 2023 International Search Report and Written Opinion dated Jun. 12, 2023.
PCT/US2023/015266 filed Mar. 15, 2023 International Search Report and Written Opinion dated May 25, 2023.
U.S. Appl. No. 17/684,180, filed Mar. 1, 2022 Restriction Requirement dated May 19, 2023.
PCT/US2022/048716 filed Nov. 2, 2022 International Search Report and Written Opinion dated Feb. 24, 2023.
PCT/US2022/048722 filed Nov. 2, 2022 International Search Report and Written Opinion dated Feb. 24, 2023.
PCT/US2022/049983 filed Nov. 15, 2022 International Search Report and Written Opinion dated Mar. 29, 2023.
PCT/US2022047727 filed Oct. 25, 2022 International Search Report and Written Opinion dated Jan. 25, 2023.
Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.
U.S. Appl. No. 17/020,476, filed Sep. 14, 2020 Final Office Action dated Jan. 5, 2023.
U.S. Appl. No. 17/020,476, filed Sep. 14, 2020 Notice of Allowance dated Apr. 28, 2022.
U.S. Appl. No. 17/468,318, filed Sep. 7, 2021 Non-Final Office Action dated Apr. 12, 2023.
U.S. Appl. No. 17/471,015, filed Sep. 9, 2021 Non-Final Office Action dated Mar. 30, 2023.
U.S. Appl. No. 17/534,099, filed Nov. 23, 2021 Non-Final Office Action dated Mar. 31, 2023.
U.S. Appl. No. 17/538,911, filed Nov. 30, 2021 Non-Final Office Action dated Mar. 2, 2023.
M. Ikhsan, K. K. Tan, AS. Putra, C. F. Kong, et al., "Automatic identification of blood vessel cross-section for central venous catheter placement using a cascading classifier," 39th Annual International Conference of the IEEE Engineering in Medicine and Biology Society (EMBC). pp. 1489-1492 (Year: 2017).
U.S. Appl. No. 17/471,015, filed Sep. 9, 2021 Advisory Action dated Feb. 2, 2024.
U.S. Appl. No. 17/471,015, filed Sep. 9, 2021 Non-Final Office Action dated Mar. 28, 2024.
U.S. Appl. No. 17/534,099, filed Nov. 23, 2021 Non-Final Office Action dated Mar. 14, 2024.
U.S. Appl. No. 17/538,911, filed Nov. 30, 2021 Notice of Allowance dated Mar. 14, 2024.
U.S. Appl. No. 17/684,180, filed Mar. 1, 2022 Advisory Action dated Apr. 4, 2024.
U.S. Appl. No. 17/722,151, filed Apr. 15, 2022 Non-Final Office Action dated Mar. 25, 2024.
U.S. Appl. No. 17/894,460, filed Aug. 24, 2022 Advisory Action dated Apr. 4, 2024.
U.S. Appl. No. 17/894,460, filed Aug. 24, 2022 Final Office Action dated Jan. 31, 2024.
U.S. Appl. No. 18/238,281, filed Aug. 25, 2023 Non-Final Office Action dated Mar. 22, 2024.
U.S. Appl. No. 17/684,180, filed Mar. 1, 2022 Non-Final Office Action dated May 8, 2024.
U.S. Appl. No. 17/722,111, filed Apr. 15, 2022 Final Office Action dated Jul. 12, 2024.
U.S. Appl. No. 17/979,564, filed Nov. 2, 2022 Non-Final Office Action dated Jun. 5, 2024.
U.S. Appl. No. 18/238,281, filed Aug. 25, 2023 Notice of Allowance dated Jul. 16, 2024.
PCT/US2022/045372 filed Sep. 30, 2022 International Search Report and Written Opinion dated Jan. 14, 2023.
U.S. Appl. No. 17/957,562, filed Sep. 30, 2022 Non-Final Office Action dated Jun. 20, 2024.
U.S. Appl. No. 17/979,601, filed Nov. 2, 2022 Non-Final Office Action dated Aug. 20, 2024.

\* cited by examiner

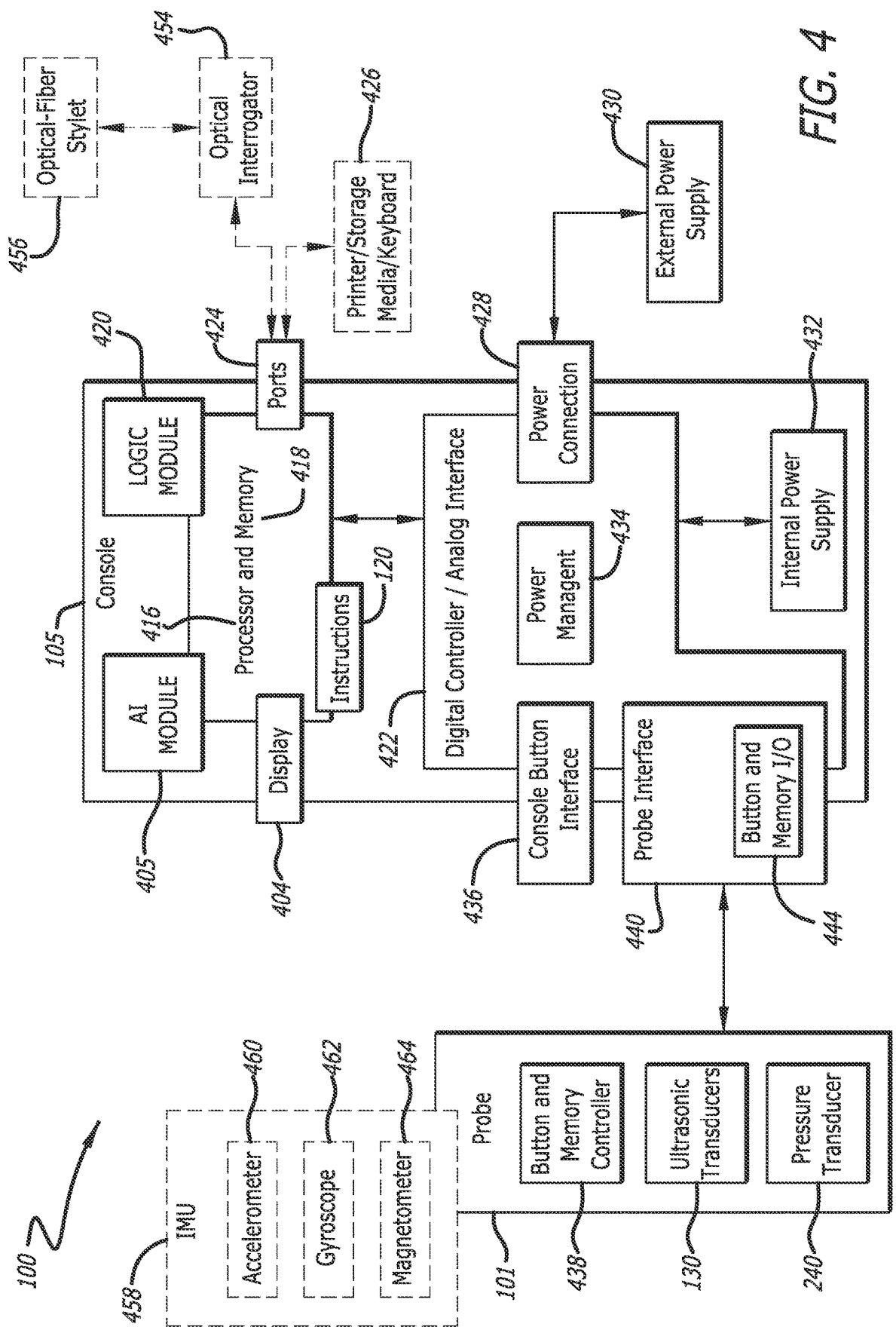

ULTRASOUND SYSTEM WITH PRESSURE AND FLOW DETERMINATION CAPABILITY

PRIORITY

This application claims the benefit of priority to U.S. Provisional Application No. 63/120,053, filed Dec. 1, 2020, which is incorporated by reference in its entirety into this application.

BACKGROUND

There is currently a variety of existing ultrasound systems that include wired or wireless ultrasound probes connected to visual displays. These systems may be used by a clinician to hold and manipulate the ultrasound probe to place a vascular access device (VAD) such as a catheter in a patient. Ultrasound imaging is commonly used for guiding a needle to targets such as veins of the patient. The needle may be monitored in real-time prior to and after a percutaneous insertion. This way a clinician may be able to determine the distance and the orientation of the needle in relation to a target vein and ensure accurate insertion with minimal discomfort to the patient. In some instances, a target vein may be difficult to distinguish from an adjacent artery. As such, in some instances, the clinician may inadvertently puncture an adjacent artery. A puncture of an artery may cause harm and/or discomfort to the patient. The arterial puncture may also require unplanned intervention by the clinician to stop bleeding from the artery. Thus, distinguishing a vein from an artery prior to needle insertion may inhibit harm and discomfort to a patient and may be logistically advantageous for the clinician.

Accordingly, disclosed herein are ultrasound imaging systems and methods that distinguish arteries from veins based on, at least, blood vessel differentiating characteristics.

SUMMARY OF THE INVENTION

Briefly summarized, disclosed herein is an ultrasound system including, an ultrasound probe comprising a plurality of ultrasound transducers configured to acquire ultrasound images. The system further includes a processor and non-transitory computer-readable medium having stored thereon a logic module that, when executed by the processor, is configured to perform operations including, receiving real-time ultrasound imaging data, detecting one or more blood vessels within the ultrasound imaging data, 1) identifying at least one blood vessel of the one or more blood vessels as an artery or 2) identifying at least one blood vessel of the one or more blood vessels a vein, and rendering a visualization of at least a subset of the one or more blood vessels on a display of the console.

In some embodiments, the processor, the non-transitory, computer-readable medium and the display screen comprise a console. In some embodiments, the ultrasound imaging system includes an operation identifying the blood vessel as an artery.

In some embodiments, the system employs at least one differentiating characteristic among a plurality of differentiating characteristics when identifying the blood vessel. The differentiating characteristics are defined by the logic module and include a blood vessel diameter, a blood vessel wall thickness, an image pulsatility of a blood vessel, a depth of a blood vessel with respect to a skin surface of a patient, a location of a first blood vessel in relation to a location of a blood second vessel, and a cross-sectional shape of a blood vessel.

In some embodiments, the system employs at least two differentiating characteristics when identifying the blood vessel.

In some embodiments, the logic module defines one or more thresholds employed when identifying a blood vessel.

In some embodiments, the logic module includes an operation of identifying at least one differentiating characteristic of the blood vessel within the real-time imaging data.

In some embodiments, the logic module includes an operation of comparing the real-time imaging data pertaining to a differentiating characteristic with one or more thresholds defined by the logic module resulting in a confidence level for the identification of the blood vessel.

In some embodiments, the real-time imaging data includes image pulsatility data of the blood vessel, and wherein identifying the blood vessel includes comparing the image pulsatility data to one or more image pulsatility thresholds to obtain the confidence level for the identification of the blood vessel.

In some embodiments, the ultrasound probe of the ultrasound imaging system includes a pressure sensor configured to obtain pressure pulsatility data of the blood vessel and the logic module includes an operation of receiving real-time pressure pulsatility data in coordination with receiving real-time imaging data. The logic module includes a differentiating characteristic pertaining to pressure pulsatility of a blood vessel, and an operation of the logic module includes comparing the pressure pulsatility data of the blood vessel to one or more pressure pulsatility thresholds to obtain a confidence level for the identification of the blood vessel.

In some embodiments, comparing the pressure pulsatility data is performed in combination with comparing the image pulsatility data to obtain a combined confidence level for the identification of the blood vessel.

In some embodiments, the logic module includes an operation of rendering a visualization of one or more blood vessels on the display of the console and includes rendering indicia on the display to indicate to the clinician if any of the blood vessels is an artery.

In some embodiments, the logic module includes operations of tracking a position of a needle tip in relation to the one or more blood vessels, and generating an alert to a clinician if the needle tip is positioned within a perimeter threshold of an artery. The alert may further include rendering indicia on the display that includes a text notification or an arrow indicating a direction to move the needle away from the artery.

In some embodiments, the ultrasound imaging system includes an artificial intelligence module configured to define the thresholds. In some embodiments, the artificial intelligence module may define one or more of the differentiating characteristics.

Disclosed herein is a method for identifying an artery among a plurality of blood vessels, including obtaining ultrasound images via an ultrasound imaging system. The ultrasound imaging system includes an ultrasound probe having a plurality of ultrasound transducers configured to acquire ultrasound images and a console. The console includes a processor and non-transitory computer-readable medium having stored thereon a logic module configured to perform operations. The operations include receiving real-time ultrasound imaging data, detecting one or more blood vessels within the ultrasound imaging data, identifying at least one blood vessel of the one or more blood vessels as an artery or identifying at least one blood vessel of the one or more blood vessels as a vein.

In some embodiments of the method, the operations include identifying the blood vessel as an artery.

In some embodiments of the method, the logic module includes an operation of rendering a visualization of at least a subset of the one or more blood vessels on a display of the console, wherein the subset includes the blood vessel. The rendering operation may further include rendering indicia on the display indicating that the blood vessel is an artery.

In some embodiments of the method, the operations include identifying at least one differentiating characteristic of the blood vessel within the real-time imaging data, and comparing the real-time imaging data to one or more thresholds defined by the logic module to obtain a confidence level that the blood vessel is an artery.

In some embodiments of the method, identifying a blood vessel as an artery includes, receiving image pulsatility data for the blood vessel, and comparing the image pulsatility data to one or more image pulsatility thresholds to obtain the confidence level that the blood vessel is an artery.

In some embodiments of the method, the ultrasound probe further comprises a pressure sensor configured to obtain pressure pulsatility data in combination with acquiring ultrasound images, and wherein identifying a blood vessel includes, receiving pressure pulsatility data for the blood vessel, and comparing the pressure pulsatility data to one or more pressure pulsatility thresholds defined by the logic module to obtain an additional confidence level for the identification of the blood vessel.

These and other features of the concepts provided herein will become more apparent to those of skill in the art in view of the accompanying drawings and following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 4 is a block diagram of the ultrasound imaging system of FIG. 1, in accordance with some embodiments.

DETAILED DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," "upward," "downward," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. Also, the words "including," "has," and "having," as used herein, including the claims, shall have the same meaning as the word "comprising."

Lastly, in the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

Unless defined otherwise, all technical and scientific terms used herein have the same meaning as commonly understood by those of ordinary skill in the art.

Figure 1:
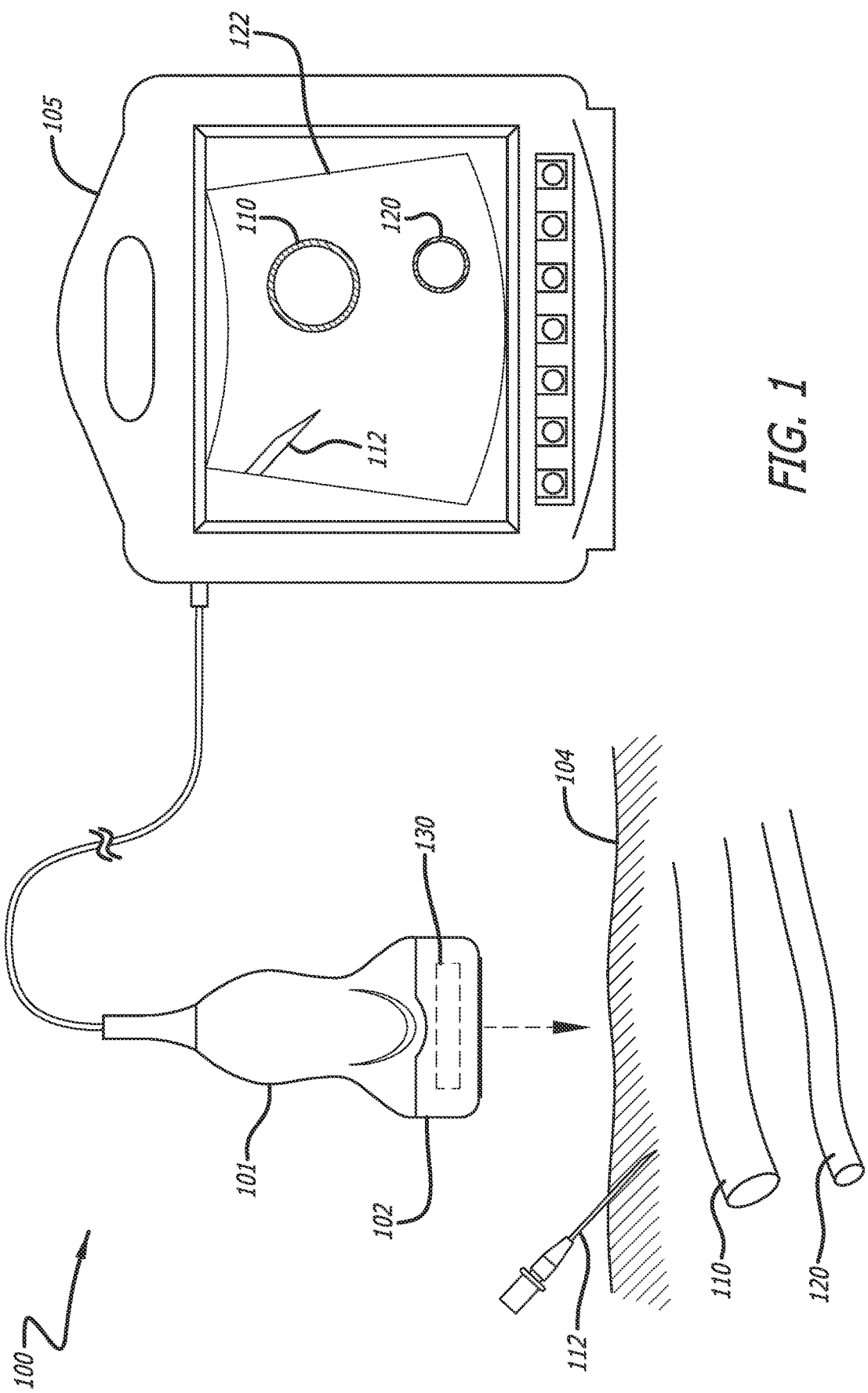
FIG. 1 illustrates an ultrasound imaging system including an ultrasound probe connected to an image processing device, in accordance with some embodiments.

FIG. 1 illustrates an ultrasound imaging system 100 including an ultrasound probe 101 connected to console 105, in accordance with some embodiments. In this embodiment, the ultrasound probe 101 is connected to the console 105 over a wired connection. In other embodiments, a wireless connection may be used. The ultrasound probe 101 includes a body that may house a console (FIG. 4) operatively connected to the console 105. The ultrasound probe 101 may be configured to assist a user such as a clinician with insertion of an access device such as a needle 112 into a target of a patient such as the vein 110.

Ultrasonic transducers 130 located in a probe head 102 of the ultrasound probe 101 are configured to capture 2-D ultrasound images to be visualized on a display of the console 105 in an ultrasound image window 122. The ultrasonic transducers 130 may be arranged and/or activated in a linear array or a 2-D array. The ultrasonic transducers 130 may be implemented as piezoelectric transducers or capacitive micro-machined ultrasonic transducers (CMUTs). When the ultrasound probe 101 is configured with the 2-D array of the ultrasonic transducers 130, a subset of the ultrasonic transducers may be linearly activated as a linear array as may be beneficial for ultrasound imaging based on ultrasound-imaging data being captured. The ultrasound transducers 130 may be configured to maintain the target, such as the vein 110, in an image plane parallel to a medical-device plane or switch to a different image plane perpendicular to the medical-device plane. In some embodiments, the ultrasound probe 101 may be configured with the moveable linear array of the ultrasonic transducers 130 that may be activated for ultrasound imaging.

In use, the probe head 102 may be placed against the skin 104 of a patient proximate to a needle-insertion site so the activated ultrasonic transducers 130 in the probe head 102 may generate and emit the ultrasound signals into the patient as a sequence of pulses. Transmitters within the probe head 102 (not shown) may receive reflected ultrasound signals (i.e., reflections of the generated ultrasonic pulses from the patient's body). The reflected ultrasound signals may be converted into corresponding electrical signals for processing into ultrasound images by a console of the ultrasound imaging system 100. Thus, a clinician may employ the ultrasound imaging system 100 to determine a suitable insertion site and establish vascular access to the target vein 110 with the needle 112 or another medical device.

As discussed above, the exemplary ultrasound imaging system 100 may be capable of detecting and identifying a vein 110 and an artery 120 and providing a visualization of veins 110 and arteries 120 in the ultrasound window 122. While a single vein 110 and a single artery 120 are shown in FIG. 1, the ultrasound imaging system 100 may be capable of obtaining ultrasound images including multiple veins 110 and arteries 120 and providing a visualization of multiple veins 110 and arteries 120 in the ultrasound window 122. As discussed above, the exemplary ultrasound imaging system 100 may provide visualization of an ultrasound image in real-time. In other words, the ultrasound imaging system 100 may provide a real-time ultrasound image in the ultrasound window 122 during an ultrasound imaging procedure.

Additionally, as will be discussed below, the ultrasound imaging system 100 may include one or more logic modules that, upon processing by a processor, are capable of processing the obtained ultrasound images, identifying one or more blood vessels (e.g., the artery 120 and the vein 110) and distinguishing the artery 120 from the vein 110. For example, the logic modules(s) of the ultrasound imaging system 100 may identify an artery 120 and distinguish the artery 120 from the vein 110 according to a plurality of differentiating characteristics. As one illustrative embodiment, the artery 120 may have a smaller diameter and a thicker wall than the vein 110, which may be detected and identified by the logic modules. As another illustrative embodiment, the artery 120 may have a higher internal pressure than the vein 110 and may have detectable variations of its diameter due to pressure pulses within the artery 120, whereas the vein 110 may have small or non-detectable pressure pulses. The ultrasound imaging system 100 may provide real-time imaging information of a blood vessel, e.g., size, cross-sectional shape, wall thickness, and movement the blood vessel or portions thereof. The ultrasound imaging system 100, via processing of the ultrasound images by the one or more logic modules, may provide detection and identification of the vein 110 and/or the artery 120 for general monitoring, diagnostics, or assessment prior to and/or post an intervention. In some embodiment, the one or more logic modules may identify fluid or body cavities (e.g., pleural space); therefore, the discussion provided herein pertaining to detection and identification of blood vessels may also apply to pleural space. It will be understood by those having skill in that art that certain embodiments described herein may only be applicable to blood vessels (e.g., distinguishing an artery from a vein).

In some embodiments, the ultrasound imaging system 100 may be configured to detect and track a position of the needle 112. In one embodiment, the ultrasound imaging system 100 may include positional tracking of the needle 112 with respect to a target, e.g., the vein 110. The clinician may adjust the position of the needle 112 for correct placement of the needle 112 in relation to the vein 110 in response to ultrasound imaging displayed in the ultrasound window 122. In some embodiments, the needle tracking can be implemented using the teachings of one or more of the following: U.S. Pat. Nos. 9,456,766, 9,492,097, 9,521,961, 9,554,716, U.S. Ser. No. 10/524,691, U.S. Ser. No. 10/449,330, and US 2018/0116551, each of which is incorporated by reference in its entirety into this application.

Figure 2:
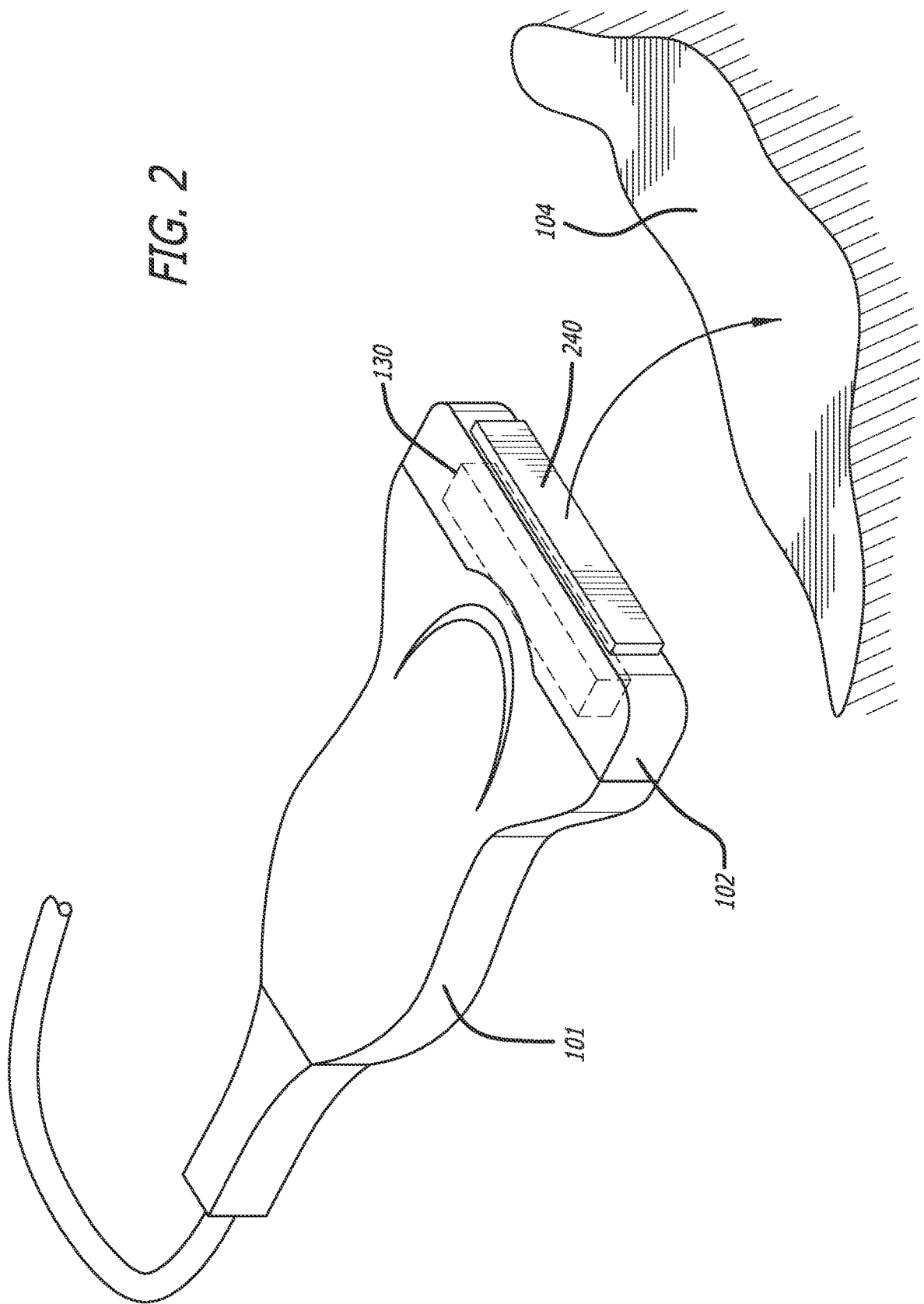
FIG. 2 is a front perspective view of an ultrasound probe assembly including a pressure sensor, in accordance with some embodiments.

FIG. 2 is a front perspective view of the ultrasound probe 101 including the probe head 102 comprising the ultrasound transducers 130. In some embodiments, the ultrasound probe 101 may include a pressure sensor 240 as a component of the probe head 102. The pressure sensor 240 may be integrated into a front surface of the probe head 102 of the ultrasound probe 101. The pressure sensor 240 may be configured to provide an indication of pressure at the skin surface. In other words, the pressure sensor 240 may indicate a pressure between the probe head 102 and the skin 104 when the clinician urges the ultrasound probe 101 against the skin 104. In some embodiments, the pressure sensor 240 may detect pressure pulses originating beneath the skin surface. In other words, a pressure pulse within the artery 120 may travel through body tissue from the artery 120 to the surface of the skin 104 to be detected by the pressure sensor 240. In some embodiments, the pressure sensor 240 may comprise one or more pressure or force transducers. In other embodiments, the pressure sensor 240 may comprise one or more of a strain gauge, a piezo-resistive strain gauge, a capacitive gauge, an electromagnetic gauge, an optical sensor, or any other suitable device for converting pressure at the probe head 102 into an electrical signal. The pressure sensor 240 may be coupled to the console to provide electrical signals to the console.

Figure 3A:
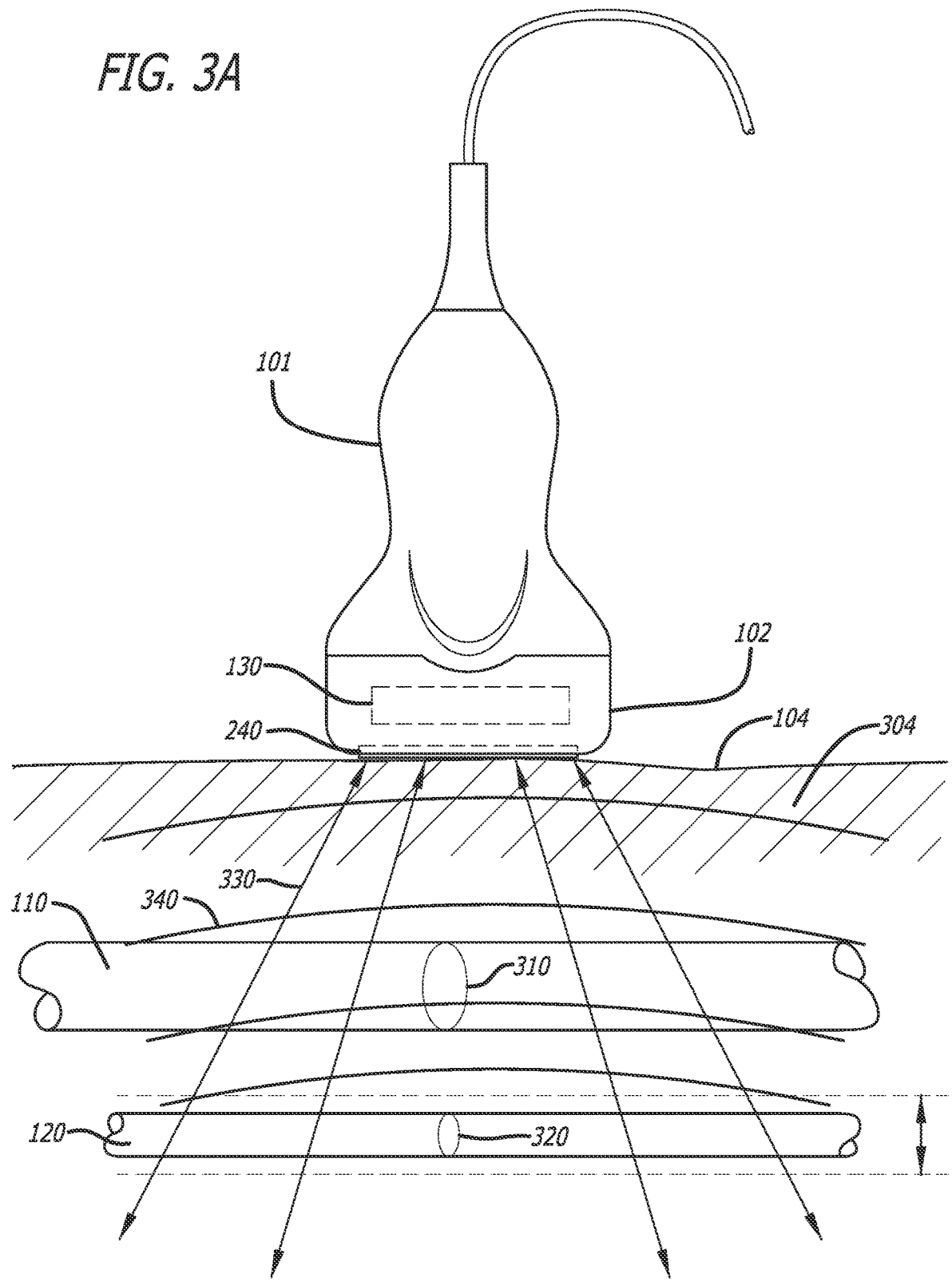
FIG. 3A illustrates the ultrasound probe of FIG. 2 together with a cross-sectional portion of a patient, in accordance with some embodiments.

FIG. 3A is a side view illustration of the ultrasound probe 101 projecting ultrasound signals 330 through the skin 104 and body tissue 304 of a patient to the vein 110 and the artery 120. As discussed above, the probe head 102 comprises ultrasound transducers 130 and a pressure sensor 240. As shown in this exemplary illustration, the vein 110 has a cross-sectional diameter 310 that is larger diameter than a cross-sectional of diameter 320 of the artery 120. As may be anatomically typical, the artery 120 is illustrated at a greater depth from the skin 104 than the vein 110. The difference in depth between the artery 120 and the vein 110 may be used as a differentiating characteristic between the artery 120 and the vein 110. The artery 120 has a higher internal pressure than the vein 110 and pulsating blood pressure within the artery 120 causes the diameter 320 of the artery 120 to expand as shown by an arrow and the dotted lines depicting the pulsatility of the artery 120. Changes of the diameter 320 in real-time may be used for identification of the artery 120 and/or for distinguishing the artery 120 from the vein 110 via processing of the ultrasound signals 330 and pressure pulses 340, discussed below.

As described above, in some embodiments, the probe head 102 of the ultrasound probe 101 may include the pressure sensor 240 capable of and configured to detect pressure pulses 340 emanating from the artery 120. FIG. 3A illustrates the pressure pulses 340 traveling through the body tissue 304 to the surface of the skin 104 and the pressure sensor 240. In some embodiments, signals from the pressure sensor 240 may be used to distinguish the artery 120 from the vein 110. In other words, differentiating characteristics between the artery 120 and the vein 110 may include pressure pulsatility as detected by the pressure sensor 240.

Figure 3B:
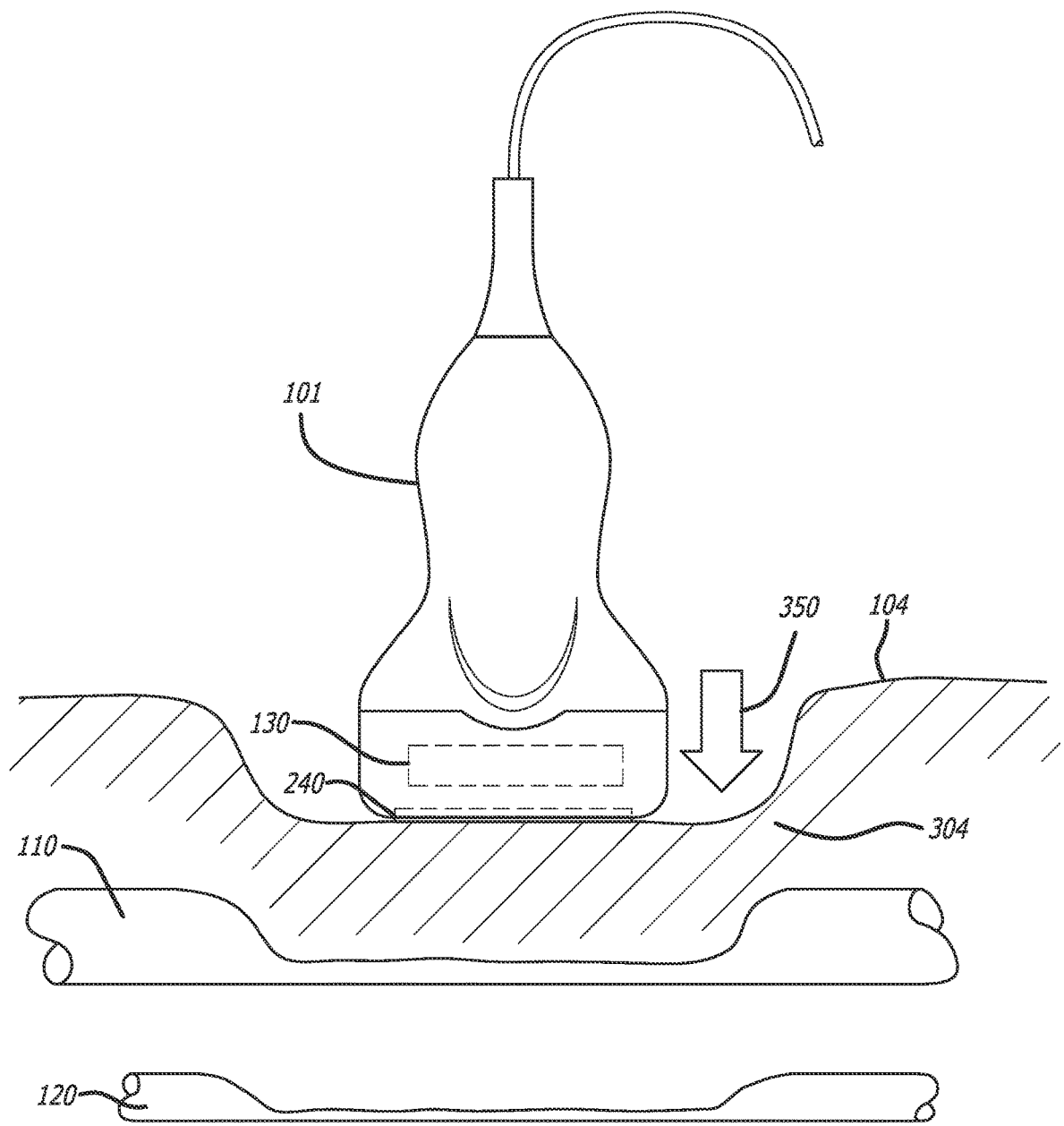
FIG. 3B illustrates the ultrasound probe of FIG. 2 together with a cross-sectional portion of a patient when a force is applied to the ultrasound probe, in accordance with some embodiments.

FIG. 3B is another side view illustration of the ultrasound probe 101 positioned in relation to the skin 104 of the patient similar to FIG. 3A. FIG. 3B differs from FIG. 3A, in that an indicated downward force is applied to the ultrasound probe 101 to provide a compression force, i.e., a compressive pressure 350, to the skin 104. In some embodiments, the compressive pressure 350 may be quantifiably measurable by the pressure sensor 240. As shown, the compressive pressure 350 translates through the body tissue 304 to the vein 110 and the artery 120 causing the vein 110 and the artery 120 to at least partially collapse. In some instances, the compressive pressure 350 may be sufficient to cause the vein 110 and/or the artery 120 to totally collapse occluding blood flow. In such an instance, the compressive pressure 350, as measured by the pressure sensor 240, may be indicative of a pressure within the vein 110 and/or the artery 120. In some embodiments, the cross-sectional shape of the vein 110 and/or the artery 120 may be detectable in the real-time ultrasound image data. In some embodiments, a difference between a compressive pressure 350 to cause the vein 110 to collapse and a compressive pressure 350 to cause the artery 120 to collapse may be a differentiating characteristic between the vein 110 and the artery 120.

In some embodiments, the logic modules of the ultrasound imaging system 100 may be configured to determine a pressure within the vein 110 and/or the artery 120 based on the pressure pulses 340 (and optionally, the ultrasound signals 330). In one instance, the compressive pressure 340 may be sufficient to cause the artery 120 to totally collapse only in the absence of a pressure pulse. In such an instance, the compressive pressure 340 as measured by the pressure sensor 240 may be indicative of a diastolic blood pressure within the artery 120. In a corresponding instance, the compressive pressure 340 may be sufficient to cause the artery 120 to totally collapse and remained collapsed throughout the pressure pulse. In this corresponding instance, the compressive pressure 340 as measured by the pressure sensor 240 may be indicative of a systolic blood pressure within the artery 120.

Referring to FIG. 4, a block diagram of the ultrasound imaging system 100 in accordance with some embodiments is shown. The console 105 may include a variety of components of the ultrasound imaging system 100. A processor 416 and memory (e.g., non-transitory, computer-readable medium) 418 such as random-access memory (RAM) or non-volatile memory, e.g., electrically erasable programmable read-only memory (EEPROM) may be included in the console 105 for controlling functions of the ultrasound imaging system 100, as well as for executing various logic operations or algorithms during operation of the ultrasound imaging system 100 in accordance with a logic module 420 stored in the memory 418 for execution by the processor 416. For example, the console 105 may be configured to instantiate by way of the logic module 420 one or more processes for adjusting 1) a distance of activated ultrasonic transducers 130 from a predefined target, e.g., a target vein 110 or area, or 2) an orientation of the activated ultrasonic transducers 130 with respect to the predefined target or area, or 3) both the distance and the orientation of the activated ultrasonic transducers 448 with respect to the predefined target or area. Additional operations of the logic module(s) 420 upon execution by the processor 416 are discussed below. The console 105 may also be configured to process electrical signals from the ultrasound probe 101 into ultrasound images. The activated ultrasonic transducers 130 may be adjusted using ultrasound-imaging data, magnetic-field data, shape-sensing data, or a combination thereof received by the console 105. The console 105 may activate certain ultrasonic transducers of a 2-D array of the ultrasonic transducers 130 or converting the already activated transducers into a linear array of the ultrasonic transducers 130.

A digital controller/analog interface 422 may be included with the console 105 and be in communication with both the processor 416 and other system components to govern interfacing between the ultrasound probe 101 and other system components set forth herein. The ultrasound imaging system 100 further includes ports 424 for connection with additional components such as optional components 426 including a printer, storage media, keyboard, etc. The ports 424 may be implemented as universal serial bus (USB) ports, though other types of ports can be used for this connection or any other connections shown or described herein. A power connection 428 is included with the console 105 to enable operable connection to an external power supply 430. An internal power supply 432 (e.g., a battery) may also be employed either with or exclusive of the external power supply 430. Power management circuitry 434 is included with the digital controller/analog interface 422 of the console 105 to regulate power use and distribution. Optionally, a stand-alone optical interrogator 454 may be communicatively coupled to the console 105 by way of one of the ports 424. Alternatively, the console 105 may include an optical interrogator integrated into the console 105. Such an optical interrogator may be configured to emit input optical signals into a companion optical-fiber stylet 456 for shape sensing with the ultrasound imaging system 100. The optical-fiber stylet 456, in turn, may be configured to be inserted into a lumen of a medical device such as the needle 112 (FIG. 1) and may convey the input optical signals from the optical interrogator 454 to a number of fiber Bragg grating (FBG) sensors along a length of the optical-fiber stylet 456. The optical interrogator 454 may be also configured to receive reflected optical signals conveyed by the optical-fiber stylet 456 reflected from the number of the FBG sensors, the reflected optical signals may be indicative of a shape of the optical-fiber stylet 456.

The optical interrogator 454 may be configured to convert the reflected optical signals into corresponding electrical signals for processing by the console 105 into distance and orientation information with respect to the target and for dynamically adjusting a distance of the activated ultrasonic transducers 130, an orientation of the activated ultrasonic transducers 130, or both the distance and the orientation of the activated ultrasonic transducers 130 with respect to the target (e.g., the target vein 110, depicted in FIG. 1) or the medical device (e.g., the needle 112, also see FIG. 1) when it is brought into proximity of the target. For example, the distance and orientation of the activated ultrasonic transducers 130 may be adjusted with respect to the vein 110 as the target. An image plane may be established by the activated ultrasonic transducers 130 being perpendicular or parallel to the vein 110 based on the orientation of the vein 110. In another example, when a medical device such as the needle 112 is brought into proximity of the ultrasound probe 101, an image plane can be established by the activated ultrasonic transducers 130 being perpendicular to a medical-device plane including the needle 112. The distance and orientation information may also be used for displaying an iconographic representation of the medical device on the display 404.

The display 404 may be integrated into (or connected to) the console 105 to provide a graphical user interface (GUI) and display information for a clinician in a form of ultrasound images acquired by the ultrasound probe 101. In addition, the ultrasound imaging system 100 may enable the distance and orientation of a magnetized medical device such as the needle 112 to be superimposed in real-time atop an ultrasound image, thus enabling the clinician to accurately guide the magnetized medical device toward an intended target (e.g., the vein 110) and/or away from an artery 120 (FIG. 1). As discussed above, the display 404 may alternatively be separate from the console 105 and communicatively (e.g., wirelessly) coupled thereto. A console button interface 436 may be used to selectively call up a desired mode to the display 404 by the clinician for assistance with an ultrasound-based medical procedure. In some embodiments, the display 404 may be implemented as an LCD device. The ultrasound probe 101 may optionally include an internal measurement unit (IMU) 458 that may house and accelerometer 460, a gyroscope 462, and a magnetometer 464.

The ultrasound probe 101 may be employed in connection with ultrasound-based visualization of a target such as the vein 110 (FIG. 1) in preparation for inserting the needle 112 or another medical device into the target. Such visualization gives real-time ultrasound guidance and assists in reducing complications typically associated with such insertion, including inadvertent arterial puncture (e.g., of the artery 120), hematoma, pneumothorax, etc. The ultrasound probe 101 may be configured to provide to the console 105 electrical signals corresponding to the ultrasound-imaging data, the magnetic-field data, the shape-sensing data, or a combination thereof for the real-time ultrasound needle guidance.

As stated above, the ultrasound probe 101 includes ultrasonic transducers 130 (see FIG. 1) and a pressure sensor 240 (see FIG. 2). The ultrasound probe 101 may further include a button and memory controller 438. The ultrasound probe 101 may be coupled to the console 105 via a probe input/output (I/O) interface 440 including a button and memory (I/O) interface 444.

The ultrasound imaging system 100 includes at least one logic module 420 configured to perform various operations when executed by the processor 416. The logic module 420 may, when executed by the processor 416, perform operations including receiving ultrasound imaging data, detecting one or more blood vessels within the ultrasound imaging data, identifying a blood vessel as an artery, and generating a visualization from the ultrasound image that renders the blood vessel as an artery. The operation may further include generating an alert indicating to a clinician that a procedure may need to be halted or adjusted, such as a needle insertion procedure, to prevent puncturing an artery, for example.

Identifying of a blood vessel as an artery may include comparing imaging data for the blood vessel with thresholds stored in the memory 418 pertaining to arteries and/or veins. The logic module 420 may further define a result of the comparison that the blood vessel is an artery or a vein according to a level of confidence. In some embodiments, indicia rendered on the display may include the level of confidence, such as 90% confidence, for example.

In one embodiment, a logic module 420 may be configured to detect a blood vessel size such as a cross-sectional diameter of the blood vessel. The logic module 420 may further compare the size of the vessel to one or more thresholds pertaining to the blood vessel diameter of arteries and/or veins. The logic module 420 may further define a result of the comparison that the blood vessel is an artery or a vein according to a level of confidence.

In one embodiment, a logic module 420 may be configured to detect a vessel wall thickness. The logic module 420 may further compare the vessel wall thickness to one or more thresholds pertaining to the blood vessel wall thicknesses of arteries and/or veins. The logic module 420 may further define a result of the comparison that the blood vessel is an artery or a vein according to a level of confidence.

In one embodiment, a logic module 420 may be configured to detect image pulsatility of a vessel, i.e., the changing of the vessel diameter due to pressure pulsing within the blood vessel. The logic module 420 may further compare the image pulsatility to one or more thresholds pertaining to the image pulsatility of arteries and/or veins. The logic module 420 may further define a result of the comparison that the blood vessel is an artery or a vein according to a level of confidence.

In one embodiment, a logic module 420 may be configured to detect a depth of the blood vessel with respect to the skin surface of the patient. The logic module 420 may further compare the depth to one or more thresholds pertaining to the depth of arteries and/or veins. The logic module 420 may further define a result of the comparison that the blood vessel is an artery or a vein according to a level of confidence.

In one embodiment, a logic module 420 may be configured to detect a difference in depth between a first blood vessel and a second blood vessel. The logic module 420 may further compare the depth difference to one or more thresholds pertaining to the depth of arteries with respect to the depth of veins. The logic module 420 may further define a result of the comparison that the blood vessel is an artery or a vein according to a level of confidence.

In one embodiment, a logic module 420 may be configured to detect a cross-sectional shape of a blood vessel. In some instances, a cross-sectional shape of a vein may be non-round, i.e., oval or flattened, due to the lower pressure within veins, contact with bones or other structure within the body, etc. By way of contrast, the pressure within an artery may generally cause the cross-sectional shape of an artery to be substantially round. The logic module 420 may further compare the cross-sectional shape to one or more thresholds pertaining to the cross-sectional shapes of veins and/or arteries. The logic module 420 may further define a result of the comparison that the blood vessel is an artery or a vein according to a level of confidence.

In some embodiments, a logic module 420 may be configured to identify a blood vessel as an artery or as a vein based on one or more differentiating characteristics of the blood vessel within an anatomical frame of reference, wherein the anatomical frame of reference may include an ultrasound image that renders visualization of the blood vessel in relation to other anatomical characteristics such as bones, tendons, ligaments, organs, a shape of an extremity, a skin surface, and/or other blood vessels, for example. In some embodiments, a logic module 420 may be configured to further identify the blood vessel as an artery or as a vein and/or obtain a greater level of confidence by changing the anatomic frame of reference. Changing the anatomic frame of reference may include altering the visualization to include more or fewer other anatomical characteristics and/or generating the ultrasound image at a different angle relative to the blood vessel or fluid or body cavities (e.g., pleural space).

In one embodiment, a logic module 420 may be configured receive pressure pulsatility data detected by the pressure sensor 240 at the skin surface, and thereby, detect a pressure pulsatility of a blood vessel. The logic module 420 may further compare the pressure pulsatility to one or more thresholds pertaining the pressure pulsatility of arteries and/or veins. The logic module 420 may further define a result of the comparison that the blood vessel is an artery or a vein according to a level of confidence.

In one embodiment, a logic module 420 may be configured receive contact pressure data detected by the pressure sensor 240 at the skin surface, the contact pressure data reflecting a compressive pressure of the probe head 102 (see FIG. 3B) against the skin surface. The logic module 420 may detect a cross-sectional shape of a blood vessel in combination with the detection of the compressive pressure. The logic module 420 may further compare the cross-sectional shape of the blood vessel, when a compressive pressure is applied, to one or more thresholds pertaining to the cross-sectional shape of veins and/or arteries when a compressive pressure is applied. The logic module 420 may further define a result of the comparison that the blood vessel is an artery or a vein according to a level of confidence.

In one embodiment, a logic module 420 may be configured to receive needle-tracking imaging data in combination with identifying a blood vessel. In some embodiments, the logic module 420 may utilize needle tracking to facilitate selection of a blood vessel as a target, such as a target vein. In some embodiments, the clinical may select the target blood vessel by positioning the needle 112 in close proximity to the target blood vessel, i.e., within a predetermined threshold distance from the target blood vessel. Once selected, the logic module 420 may provide feedback to the clinician that the target blood vessel is selected, which feedback may include rendering visualization indicia indicating that the target blood vessel is selected.

In some embodiments, the logic module 420 may detect a position of a tip of the needle 112 (see FIG. 1) with respect to an identified artery. The logic module 420 may further compare the position of the tip to one or more thresholds pertaining to a perimeter of the identified artery, such a safe distance away from the identified artery, for example. The logic module 420 may further generate feedback to the clinician if the position of the needle tip exceeds a perimeter threshold. In some embodiments, the feedback may include rendering visual indicia, such as a text notification or an arrow indicating a direction to move the needle 112, for example. As may be appreciated by one of ordinary skill, the logic module 420 may be figured to provide other feedback to the clinician in the forms of visual indicia, audio alerts, etc., pertaining to aspects of a needle position with respect to a blood vessel, which other feedback is included in this disclosure.

The logic module 420 may combine individual confidence levels (i.e., confidence levels associated with individual differentiating characteristics) to produce a combined confidence level that is greater than any of the individual confidence levels.

The ultrasound imaging system 100 may include an artificial intelligence (AI) module 405 (which may be a sub-module of the logic module 420) that may be employed for identifying a blood vessel as an artery or a vein or otherwise distinguishing an artery from a vein. The AI module 405 may be integrated into the console 105, coupled to the console 105, or accessed remotely on a separate server. The AI module 405 may be configured to receive and process training data sets that include data pertaining to differentiating characteristics which may comprise size or diameter of the blood vessel, position of the blood vessel relative to a skin surface or other body structure, relative position between adjacent blood vessels, motion or changing diameter of blood vessel in response pressure pulsing within the blood vessel, cross-section shape of the blood vessel, cross-section shape of the blood vessel in response to applied pressure, and wall thickness of the blood vessel.

In one example, processing of the AI module 405 may include generation of a machine-learning (ML) model and training of the ML model using received one or more training data sets. The ML model may then be deployed to score ultrasound signals and/or pressure pulse data to detect and/or identify particular targets, such as blood vessels and more specifically, veins or arteries. In some embodiments, the trained ML model may be stored in the memory 418.

The AI module 405 may apply algorithms or other logic operations to define a set of thresholds for any or all of the differentiating characteristics. The AI module 405 may define an initial default set of thresholds via an initial training set of AI data. The logic module 420 may apply default thresholds defined by the AI module 405 in identifying a blood vessel as an artery or a vein or otherwise distinguishing an artery from a vein. In some instances, the AI module 405 may incorporate additional AI data to add precision to the set of thresholds or otherwise redefine a set of thresholds. In some instance, the AI module may define additional differentiating characteristics together with associated thresholds.

In some embodiments, the logic module 420 may store, monitor, and/or analyze data pertaining to confidence levels generated during comparison of real-time data with a set of thresholds. The logic module 420 may then instigate a process of incorporating additional imaging data into the AI process and generate a new and improved set of thresholds.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An ultrasound imaging system comprising:
   an ultrasound probe comprising a plurality of ultrasound transducers configured to acquire ultrasound images;
   a processor; and
   non-transitory computer-readable medium having stored thereon logic that, when executed by the processor, is configured to perform operations including:
      receiving ultrasound imaging data,
      detecting one or more blood vessels within the ultrasound imaging data,
      identifying at least one blood vessel of the one or more blood vessels as an artery or as a vein,
      rendering a visualization of at least a subset of the one or more blood vessels on a display,
      tracking a position of a needle tip in relation to the one or more blood vessels, and
      generating an alert to a clinician if the needle tip is positioned within a perimeter threshold of the artery.

2. The ultrasound imaging system of claim 1, wherein the logic that, when executed by the processor, causes performances of further operations including:
   identifying the at least one blood vessel as the artery based on at least one differentiating characteristic of a plurality of differentiating characteristics of blood vessel type.

3. The ultrasound imaging system of claim 2, wherein the at least one differentiating characteristic of the plurality of differentiating characteristics is employed when identifying a blood vessel, the plurality of differentiating characteristics comprising:
 a diameter of the blood vessel,
 a wall thickness of the blood vessel,
 an image pulsatility of the blood vessel,
 a depth of the blood vessel with respect to a skin surface of a patient,
 a location of the blood vessel in relation to a location of a second blood vessel, or
 a cross-sectional shape of the blood vessel.

4. The ultrasound imaging system of claim 3, wherein at least two differentiating characteristics are employed when identifying the at least one blood vessel.

5. The ultrasound imaging system of claim 1, wherein the logic defines one or more thresholds employed when identifying the at least one blood vessel.

6. The ultrasound imaging system of claim 5, wherein identifying the at least one blood vessel includes identifying at least one differentiating characteristic of the blood vessel within the ultrasound imaging data.

7. The ultrasound imaging system of claim 6, wherein identifying the blood vessel includes comparing the ultrasound imaging data pertaining to the at least one differentiating characteristic to one or more thresholds defined by the logic.

8. The ultrasound imaging system of claim 7, wherein a result of comparing the ultrasound imaging data to the one or more thresholds is a confidence level for identification of the at least one blood vessel.

9. The ultrasound imaging system of claim 8, wherein the ultrasound imaging data includes image pulsatility data of the blood vessel, and wherein identifying the blood vessel includes comparing the image pulsatility data to one or more image pulsatility thresholds to obtain the confidence level for the identification of the at least one blood vessel.

10. The ultrasound imaging system of claim 3, wherein the ultrasound probe comprises a pressure sensor configured to obtain pressure pulsatility data of the at least one blood vessel.

11. The ultrasound imaging system of claim 10, wherein the logic, when executed by the processor, causes performance of further operations including receiving pressure pulsatility data in coordination with receiving the ultrasound imaging data.

12. The ultrasound imaging system of claim 11, wherein the plurality of differentiating characteristics further comprises a pressure pulsatility of the at least one blood vessel.

13. The ultrasound imaging system of claim 12, wherein identifying the at least one blood vessel includes comparing the pressure pulsatility data of the at least one blood vessel to one or more pressure pulsatility thresholds to obtain a confidence level for identification of the at least one blood vessel.

14. The ultrasound imaging system of claim 13, wherein comparing the pressure pulsatility data is performed in combination with comparing image pulsatility data to obtain a combined confidence level for identification of the at least one blood vessel.

15. The ultrasound imaging system of claim 1, wherein rendering the visualization of the one or more blood vessels on the display includes rendering indicia on the display to indicate to the clinician whether the at least one blood vessel is the artery.

16. The ultrasound imaging system of claim 1, wherein generating the alert includes rendering indicia on the display that includes a text notification or an arrow indicating a direction to move the needle tip away from the artery.

17. The ultrasound imaging system of claim 1, wherein the logic includes an artificial intelligence module configured to generate and train a model for scoring the ultrasound imaging data and pressure pulsatility data in order to detect the at least one blood vessel and identify the at least one blood vessel as either the artery or the vein.

18. The ultrasound imaging system of claim 17, wherein the artificial intelligence module is further configured to utilize one or more of a plurality of differentiating characteristics.

19. An ultrasound imaging system comprising:
 an ultrasound probe comprising a plurality of ultrasound transducers configured to acquire ultrasound images;
 a processor; and
 non-transitory computer-readable medium having stored thereon logic that, when executed by the processor, is configured to perform operations including:
  receiving ultrasound imaging data,
  detecting one or more blood vessels within the ultrasound imaging data,
  identifying at least one blood vessel of the one or more blood vessels as an artery or as a vein, and
  rendering a visualization of at least a subset of the one or more blood vessels on a display,
 wherein the logic includes an artificial intelligence module configured to generate and train a model for scoring the ultrasound imaging data and pressure pulsatility data in order to detect the at least one blood vessel and identify the at least one blood vessel as either the artery or the vein.

20. The ultrasound imaging system of claim 19, wherein the logic that, when executed by the processor, causes performances of further operations including:
 identifying the at least one blood vessel as the artery based on at least one differentiating characteristic of a plurality of differentiating characteristics of blood vessel type.

21. The ultrasound imaging system of claim 20, wherein the at least one differentiating characteristic of a plurality of differentiating characteristics is employed when identifying a blood vessel, the plurality of differentiating characteristics comprising:
 a diameter of the blood vessel,
 a wall thickness of the blood vessel,
 an image pulsatility of the blood vessel,
 a depth of the blood vessel with respect to a skin surface of a patient,
 a location of the blood vessel in relation to a location of a second blood vessel, or
 a cross-sectional shape of the blood vessel.

22. The ultrasound imaging system of claim 21, wherein at least two differentiating characteristics are employed when identifying the blood vessel.

23. The ultrasound imaging system of claim 19, wherein the logic defines one or more thresholds employed when identifying the at least one blood vessel.

24. The ultrasound imaging system of claim 19, wherein identifying a blood vessel includes identifying at least one differentiating characteristic of the blood vessel within the ultrasound imaging data.

* * * * *